(12) United States Patent
Nousiainen et al.

(10) Patent No.: US 12,268,522 B2
(45) Date of Patent: Apr. 8, 2025

(54) STRAP FOR A BIOMETRIC MONITOR

(71) Applicant: PulseOn Oy, Espoo (FI)

(72) Inventors: Jari Nousiainen, Espoo (FI); Jani Mäenpää, Espoo (FI)

(73) Assignee: PulseOn Oy, Espoo (FI)

(*) Notice: Subject to any disclaimer, the term of this patent is extended or adjusted under 35 U.S.C. 154(b) by 230 days.

(21) Appl. No.: 16/607,745

(22) PCT Filed: May 3, 2018

(86) PCT No.: PCT/FI2018/050323
§ 371 (c)(1),
(2) Date: Oct. 24, 2019

(87) PCT Pub. No.: WO2018/202952
PCT Pub. Date: Nov. 8, 2018

(65) Prior Publication Data
US 2020/0146625 A1 May 14, 2020

(30) Foreign Application Priority Data

May 5, 2017 (FI) .................................... 20175399

(51) Int. Cl.
*A61B 5/00* (2006.01)
*A44C 5/14* (2006.01)
(Continued)

(52) U.S. Cl.
CPC .............. *A61B 5/681* (2013.01); *A44C 5/14* (2013.01); *A61B 5/02055* (2013.01);
(Continued)

(58) Field of Classification Search
CPC ................. A61B 5/681; A61B 5/6824; A61B 5/02438; A44C 5/14
See application file for complete search history.

(56) References Cited

U.S. PATENT DOCUMENTS

| | | | |
|---|---|---|---|
| 5,577,007 A | 11/1996 | Houlihan | |
| 6,130,862 A | 10/2000 | Upton | |

(Continued)

FOREIGN PATENT DOCUMENTS

| | | | |
|---|---|---|---|
| FR | 2357202 A1 | 2/1978 | |
| JP | H09101379 A | 4/1997 | |

(Continued)

*Primary Examiner* — Lynsey C Eiseman
*Assistant Examiner* — Jessica L Mullins
(74) *Attorney, Agent, or Firm* — Thomas|Horstemeyer LLP

(57) ABSTRACT

The present disclosure relates to a wrist strap for a biometric monitor, wherein the biometric monitor comprises a casing having a first surface and a second surface opposite to the first surface, the second surface comprising a biometric sensor area located at the centre area of the second surface, said strap comprising receiving means arranged to receive the biometric monitor, such that the biometric monitor is attachable to the strap via a pair of parts enabling rotational movement of the biometric monitor, the parts being located at two opposite perimeter side edges of the biometric monitor, and thereby defining a rotation axis, wherein the perpendicular bisector of the rotation axis between the pair of parts is arranged to pass through the centre area of the second surface. The present disclosure also provides a biometric monitor connected to the wrist strap.

10 Claims, 11 Drawing Sheets

(51) Int. Cl.
*A61B 5/0205* (2006.01)
*A61B 5/024* (2006.01)
*A61B 5/0295* (2006.01)
*A61B 5/11* (2006.01)

(52) U.S. Cl.
CPC ........ *A61B 5/02438* (2013.01); *A61B 5/0295* (2013.01); *A61B 5/1112* (2013.01); *A61B 2562/0219* (2013.01); *A61B 2562/0223* (2013.01)

(56) References Cited

U.S. PATENT DOCUMENTS

| | | |
|---|---|---|
| D447,704 S | 9/2001 | Deguines |
| 2007/0097688 A1* | 5/2007 | Gibbons ............ A44C 5/0069 362/282 |
| 2009/0257323 A1 | 10/2009 | Soltani |
| 2013/0152276 A1 | 6/2013 | Hsieh et al. |
| 2014/0121539 A1 | 5/2014 | Chatterjee et al. |
| 2014/0352023 A1* | 12/2014 | Mordecai ............ A61B 5/6804 2/69 |
| 2015/0265034 A1* | 9/2015 | Lee ............ A45F 5/00 224/219 |
| 2016/0026156 A1* | 1/2016 | Jackson ............ G06F 3/04817 368/14 |
| 2016/0192526 A1 | 6/2016 | Gao et al. |
| 2017/0231338 A1* | 8/2017 | Thomas ............ A44C 17/0216 63/1.12 |

FOREIGN PATENT DOCUMENTS

| | | |
|---|---|---|
| WO | 2009126794 A2 | 10/2009 |
| WO | 2012070986 A2 | 5/2012 |
| WO | 2015181438 A1 | 12/2015 |

* cited by examiner

STRAP FOR A BIOMETRIC MONITOR

Priority

This application is a U.S. national application of the international application number PCT/FI2018/050323 filed on May 3, 2018, which claims priority of Finnish application FI20175399 filed on May 5, 2017, the contents of all of which are incorporated herein by reference.

FIELD OF THE APPLICATION

The present application relates to a strap for a portable biometric monitor and to a portable biometric monitor comprising said strap. More particularly the present application relates to a wearable biometric monitor, such as a heart rate monitor for attaching to a wrist of a user.

BACKGROUND

Physiological data can be measured from a user by using portable biometric monitors, which may be attached to the user, for example to the wrist, forearm, or arm of the user. The physiological data may include for example heart rate. Traditional monitors usually contain a separate sensor, which is attached for example to the user's chest with a strap, and which communicates wirelessly with the wrist device. The use of separate sensors complicates the use of a portable biometric monitor, and therefore there is a need to develop solutions embedded to the wrist-attached or other extremity attached device.

One way for measuring the heart rate is using optical measurement. The optical heart rate measurement is based on the fact that light is emitted by a light source towards body tissue and at least one detector is configured to detect the intensity of reflected light after propagation through the body tissue.

In such measurement a photoplethysmogram (PPG) is obtained. It is an optically obtained plethysmogram, a volumetric measurement of an organ. A PPG is often obtained by using a pulse oximeter which illuminates the skin and measures changes in light absorption. With each cardiac cycle the heart pumps blood to the periphery. Even though this pressure pulse is somewhat damped by the time it reaches the skin, it is enough to distend the arteries and arterioles in the subcutaneous tissue. If the pulse oximeter is attached without compressing the skin, a pressure pulse can also be seen from the venous plexus, as a small secondary peak.

The change in volume caused by the pressure pulse may be detected by illuminating the skin with the light from a light-emitting diode (LED) and then measuring the amount of light either transmitted or reflected to a photodiode. Each cardiac cycle appears as a downward peak in the photodiode. Because blood flow to the skin can be modulated by multiple other physiological systems, the PPG can also be used to monitor breathing, hypovolemia, and other circulatory conditions. Additionally, the shape of the PPG waveform differs from subject to subject, and varies with the location and manner in which the pulse oximeter is attached.

There are several challenges when measuring pulse optically. The optical measurement is based on light absorption changes caused by blood flow in a lighted area. If the shape of the lighted area changes during the measurement, for example, due to movement of the pulse measuring device, the measurement is disturbed. Thus, for example, movements of a hand and of the user cause errors to the measurement in many ways.

In order to avoid problems in the measurement of biometric monitors, especially in optical measurements, the device needs to be as stable as possible in relation to skin and needs to minimize mechanical changes in tissue area during movement. This is especially important during activities, such as sports-related activities and workouts, and when the biometric monitoring device is used as an athletic performance or fitness monitor.

The wrists of different users may vary in size ranging in perimeter for example from 12 cm to over 20 cm. This makes it very challenging to optimize the contact of the portable biometric monitor for use with all or most of the users, as the devices are usually produced in one size only.

There are some ways to address the above problems. One solution is to tighten a strap of the measuring device. The problem, however, is that a user may tighten the strap too much, which in turn is uncomfortable and prevents blood flow in tissue. In turn, too loose tightening of the strap allows the portable measuring device to move too much in relation, for example, to a wrist and body tissue. Further, too complicated tightening and setting procedure makes the device less convenient to use.

One type of personal portable biometric devices include a silicone wrist band and a heart rate monitor module embedded into the wrist band. In such devices the biometric monitor is mechanically an integral part of the wrist band and therefore the contact of the skin with the optical sensor in the module is greatly affected by the movement of the wrist band.

SUMMARY

One embodiment provides a wrist strap for a biometric monitor, wherein the biometric monitor comprises a casing having a first surface and a second surface opposite to the first surface, the second surface comprising a biometric sensor area located at the centre area of the second surface, said strap comprising receiving means arranged to receive the biometric monitor, such that the biometric monitor is attachable to the strap via a pair of parts enabling rotational movement of the biometric monitor, the parts being located at two opposite perimeter side edges of the biometric monitor, and thereby defining a rotation axis (Ax1), wherein the perpendicular bisector of the rotation axis (Ax1) between the pair of parts is arranged to pass through the centre area of the second surface.

One embodiment provides a wrist strap for a biometric monitor, wherein the biometric monitor comprises a casing having a first surface and a second surface opposite to the first surface, the second surface comprising a biometric sensor area located at the centre area of the second surface, said strap comprising receiving means arranged to receive the biometric monitor, such that the biometric monitor is attachable to the strap via two pair of parts enabling rotational movement of the biometric monitor, the parts of each pair of parts being located at two opposite perimeter side edges of the biometric monitor, the two pair of parts thereby defining two parallel rotation axes (Ax1, Ax2), wherein the perpendicular bisectors of the two parallel rotation axes (Ax1, Ax2) between the two pairs of parts is arranged to pass through the centre area of the second surface.

One embodiment provides a wrist strap for a biometric monitor, wherein the biometric monitor comprises a casing having a first surface and a second surface opposite to the first surface, the second surface comprising a biometric sensor area located at the centre area of the second surface, said strap comprising a frame in an aperture in the strap arranged to receive the biometric monitor, the frame being connected to the strap via a pair of elastic parts enabling rotational movement of the biometric monitor, the parts being located at two opposite perimeter side edges of the biometric monitor, and thereby defining a rotation axis (Ax1), wherein the perpendicular bisector of the rotation axis (Ax1) between the pair of parts is arranged to pass through the centre area of the second surface.

One embodiment provides a biometric monitor comprising a casing having a first surface and a second surface opposite to the first surface, the second surface comprising a biometric sensor area located at the middle or centre of the second surface, wherein the biometric monitor is connected to the strap described herein.

One embodiment provides a biometric monitor connected to a wrist strap, wherein the biometric monitor comprises a casing having a first surface and a second surface opposite to the first surface, the second surface comprising a biometric sensor area located at the centre area of the second surface, said strap comprising a frame in an aperture in the strap arranged to receive the biometric monitor, the frame being connected to the strap via a pair of elastic parts enabling rotational movement of the biometric monitor, the parts being located at two opposite perimeter side edges of the biometric monitor, and thereby defining a rotation axis (Ax1), wherein the perpendicular bisector of the rotation axis (Ax1) between the pair of parts passes through the centre area of the biometric monitor. In one example the perpendicular bisector of the rotation axis (Ax1) between the pair of parts passes through the biometric sensor area.

One embodiment provides a wrist strap 10 for a biometric monitor, wherein the biometric monitor comprises a casing 12 having a first surface 14 and a second surface 16 opposite to the first surface, the second surface comprising a biometric sensor area 18 located at the centre area of the second surface the centre area having a diameter in the range of 5-20 mm, said strap comprising receiving means arranged to receive the biometric monitor, such that the biometric monitor is attachable to the strap via a pair of parts 20, 21; 22, 23; 24, 25 enabling rotational movement of the biometric monitor, the parts being located at two opposite perimeter side edges of the biometric monitor, and thereby defining a rotation axis Ax1, the rotation axis extending in a first direction which is a perpendicular direction to the direction of the strap, wherein the perpendicular bisector PB1 of the rotation axis Ax1 between the pair of parts is arranged to pass through the centre area of the second surface, wherein the receiving means comprises a frame in an aperture in the strap connected to the strap via the pair of parts.

One embodiment provides a biometric monitor connected to a wrist strap, wherein the biometric monitor comprises a casing having a first surface and a second surface opposite to the first surface, the second surface comprising a biometric sensor area located at the centre area of the second surface, said strap comprising receiving means comprising apertures arranged to receive two pair of parts in form of pivots in the biometric monitor, such that the biometric monitor is attachable to the strap via the two pair of parts enabling rotational movement of the biometric monitor, the parts of each pair of parts being located at two opposite perimeter side edges of the biometric monitor, the two pair of parts thereby defining two parallel rotation axes (Ax1, Ax2), wherein the perpendicular bisectors of the two parallel rotation axes (Ax1, Ax2) between the two pairs of parts pass through the centre area of the second surface. In one example the perpendicular bisectors of the two parallel rotation axes (Ax1, Ax2) between the two pairs of parts pass through the biometric sensor area.

The aspects of the invention are characterized in the independent claims. Various embodiments are disclosed in the dependent claims. The features recited in dependent claims and in the embodiments are mutually freely combinable unless otherwise explicitly stated.

The construction of the portable biometric monitor enables efficient packing of the electronics inside the casing. As the pair of parts acting as hinges and providing the rotational movement do not have axles reaching through the whole casing of the device, there is more room for the electronics, sensors, displays, mechanics and the like. This has an effect of enabling more compact design on the device, which helps for example controlling the contact of the device with the user and making the wearing more comfortable due to small size. With a compact device the attachment of the strap to the device itself may be implemented for example in a way which enables the attachment points being close to each other.

As the strap is connected to the body of the monitor with the pair of parts providing the rotational movement, which may be also called as hinged movement, which are positioned to provide the axis of movement at the centre of the monitor, the movement of the user, for example the movement of the wrist of the user, has less disturbance to the contact of the device with the user. The rotational movement refers to the movement, i.e. rotation, of the biometric monitor, more particularly the casing, the housing or the module forming the biometric monitor, along the one rotation axis or the two rotation axes.

The hinged structure described in the embodiments prevents the monitor, casing or module from pivoting up at one end when the user's wrist moves or turns, or if the strap tends to rotate or move in the wrist, as is the case with conventional rigid structures. The hinged structure provides an effect of adapting the wrist strap to the rotating movements and shapes of different types of wrists. The mechanical behavior of the structure is made short, i.e. the effective length of the biometric monitor attached to the strap is shorter than the actual length of the monitor. As there are different types of wrists having different dimensions and angles, the pivoted structure may turn even about 90 degrees independently at each end, thus adapting to the contour of the user's wrist. This minimizes the leverage effect directed to the strap attachment caused by the movements of the wrist. The force required for lifting the monitor is maximized and simultaneously the force required for maintaining the position of the monitor is minimized.

This provides an effect of enhancing the contact of the device and the sensor with the skin of the user and maintaining an unchanged position of the monitor, more particularly the sensor part, on the wrist. If the pairs of parts in the case of two pairs of parts were more far away from each other, said movements would move the device body in a way which would break the contact of the sensor with the skin.

The rotational movement of the casing enables wrist movements without disturbing the contact of the device with the skin. This provides an effect of enhancing the contact of the device and the sensor with the skin of the user. It was found out that when the rotation axis, or the two rotation axes in the case of two pairs of parts, are above the sensor area the movement of the biometric monitor attached to the wrist strap had little or no effect to the function of the biometric sensor. The sensor area maintains its contact with the skin.

The design of the strap attachment to the body of the monitor has an effect of reducing the pressure of the device against the skin, and at the same time enhancing the stability of the device on the skin. The enhanced stability and the enhanced contact provide an effect of reducing the changes in the pressure, angle and movement of the device, which enhances the measuring accuracy, especially with optical sensors. Also this provides enhanced convenience of use of the device as there is no need to overtighten the strap. If a stretchable strap is used the design enables immediate stability and contact of the device with the user's skin already without further adjustment of the strap. This provides an effect of allowing the slipping of the device to a wrist and starting the use thereof immediately thus saving time and allowing convenient use.

The feature that the pair of parts, such as pivots or the like, do not penetrate into the housing has an effect of providing a reliable and solid construction of the device. Also a device constructed in a modular casing having no external or protruding parts enables obtaining the same effects. Such constructions are also water-proof with no need for any further sealing.

DETAILED DESCRIPTION

Figure 1:
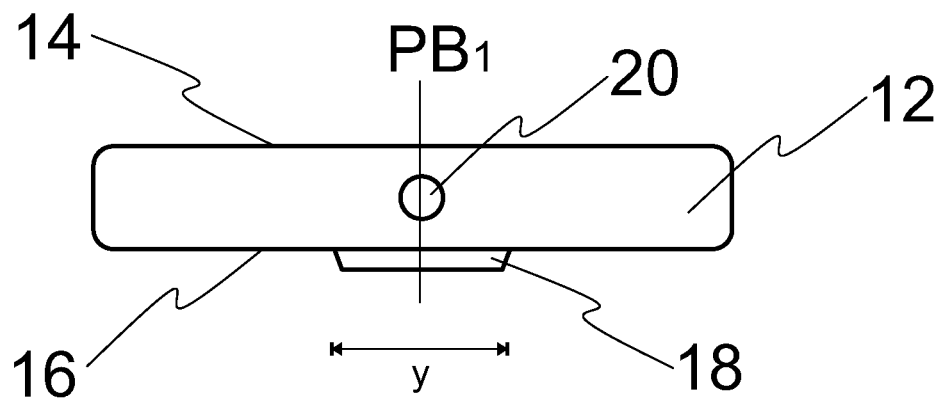
FIG. 1 shows a schematic side view of a biometric monitor having one pair of parts

Biometrics refers to metrics related to human characteristics. Biometric identifiers are distinctive, measurable characteristics used to label and describe individuals. Biometric identifiers may comprise physiological data. The biometric monitor described herein is arranged to monitor or measure one or more of such biometric identifiers from an individual user, such as to detect, collect, save and/or process such information. The biometric monitor may be arranged to output one or more results from such one or more measurements.

The biometric monitor comprises a casing 12 having a first surface 14 and a second surface 16 opposite to the first surface, the second surface comprising a biometric sensor area 18 located at the centre or the centre area of the second surface. The casing may be also called as a housing or a module. The portable biometric device contains all the components installed in the casing 12, i.e. the biometric device contains only one casing. Such a device may be also called as a module. No wired external parts or modules are connected to the casing. The components in the casing 12 may include one or more biometric sensor(s), one or more processor(s), one or more input means, such as buttons, touch-sensitive parts or the like, a power source, optionally a display, memory, a transmitter and/or receiver, and/or an antenna, all operatively and/or physically connected together inside the casing and installed in the casing. The casing is a compact casing, such as wrist size casing or other wearable casing configured to be installed with a strap to a user. In most cases the casing is a flat or substantially flat casing. The casing is usually closed. The casing has a first surface and a second surface, usually wherein the distance of the surfaces is shorter than the shortest diameter of the surface. The first surface and the second surfaces may be also called as first side and a second side. The second surface is the surface which is against skin when the device is in use, i.e. installed to a wrist. The first surface is the visible surface, and it may contain a display and/or one or more light sources, for example LEDs which indicate one or more function(s) of the device. The casing or the module may contain one or more fastening means for fastening the casing or the module to a strap, such as pivots, apertures, or the like, or the casing or the module may be provided as having no fastening means. The latter device may be arranged to be installed into an aperture in a wrist band designed to receive the casing or module. Designed to receive means that the object designed to receive contains such shaping or such parts that fit to the corresponding shapes or parts in the object to be received. The object which is received may be locked or otherwise attached to the receiving object.

The flat casing may be round or circular, for example as shown in FIGS. 15-18, or oval, or it may be angular, for example having four sides, such as square shaped or tetragonal, as shown in FIGS. 1-12 and 19-20.

The biometric monitor is connected to a strap 10 for attaching to a user. In one embodiment the strap is a wrist strap. Other examples of the straps include forearm straps, ankle straps, forehead straps, tights straps, leg straps, arm straps and neck straps. However, the dimensions used in the embodiments herein are optimized mainly for wrist straps for different wrist sizes.

The strap comprises receiving means arranged to receive the biometric monitor, more particularly a compatible biometric monitor, which may be configured to be connected to the strap, i.e. the monitor and the strap have compatible parts. The biometric monitor is removably attached or attachable to the strap, so that a user may remove the monitor casing from the strap, and/or attach the monitor casing to the strap. This enables for example changing the strap, or for example removing the monitor casing for maintenance, such as for battery replacement.

The receiving means are arranged such that the biometric monitor is attachable to the strap 10 via at least one pair of parts (20, 21; 22, 23; 24, 25). The pair of parts may be connected to the receiving means or the receiving means may form the pair of parts or a part of the pair of parts. The pair of parts may be directly attached to the monitor casing, or the monitor casing may be placed into a separate receiving part, such as a frame or the like, which is connected to the pair of parts. Such a separate receiving part enables providing rotational movement to a biometric monitor embedded into a strap, such as a silicone strap, and therefore enhances the contact of the sensor with skin in such devices.

The pair of parts (20, 21; 22, 23; 24, 25) enable a hinged movement of the biometric monitor. The rotational movement refers to a movement, such as rotating movement or rotation along a rotation axis, which may take place when the biometric monitor is attached to the strap, for example when attached to a wrist during the user movement. The rotational movement is designed to maintain the contact of the biometric sensor with the skin of the user.

Figure 5:
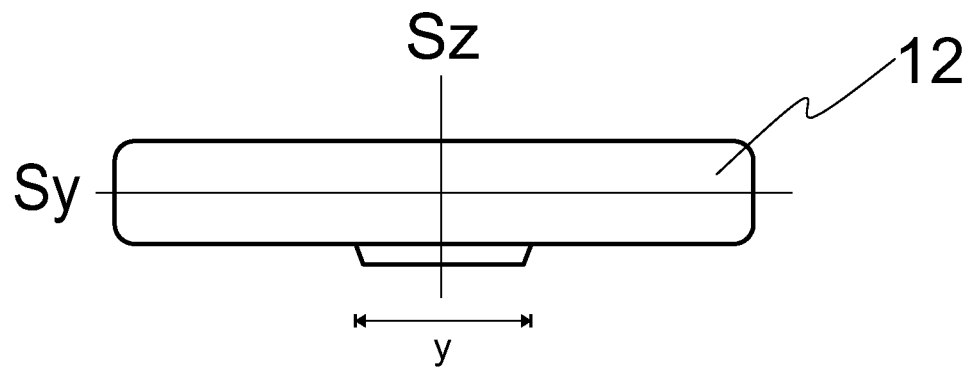
FIG. 5 shows a schematic side view of a biometric monitor having two pairs of parts
Figure 6:
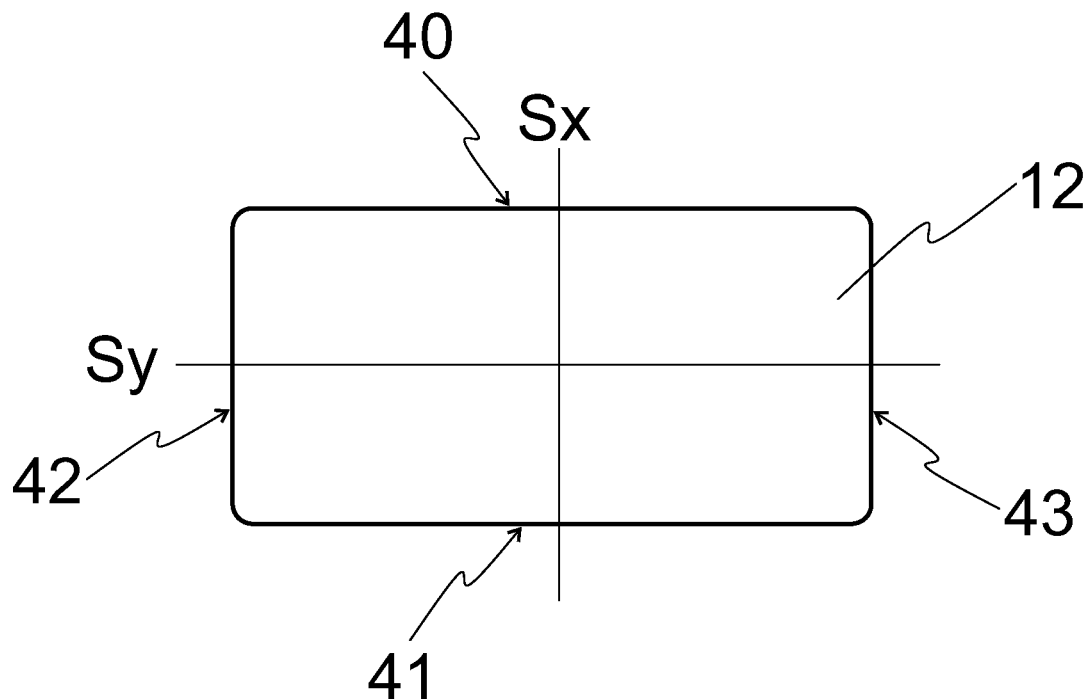
FIG. 6 shows a schematic view of a biometric monitor having two pairs of parts seen from the sensor area side
Figure 7:
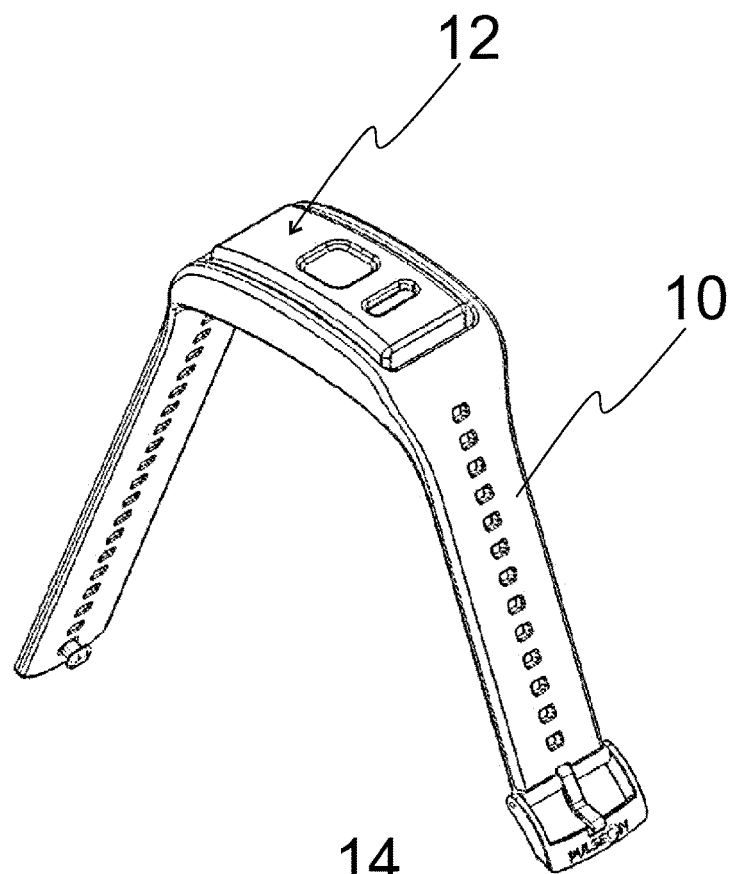
FIG. 7 shows an example of a biometric monitor attached to a silicone wrist strap
Figure 8:
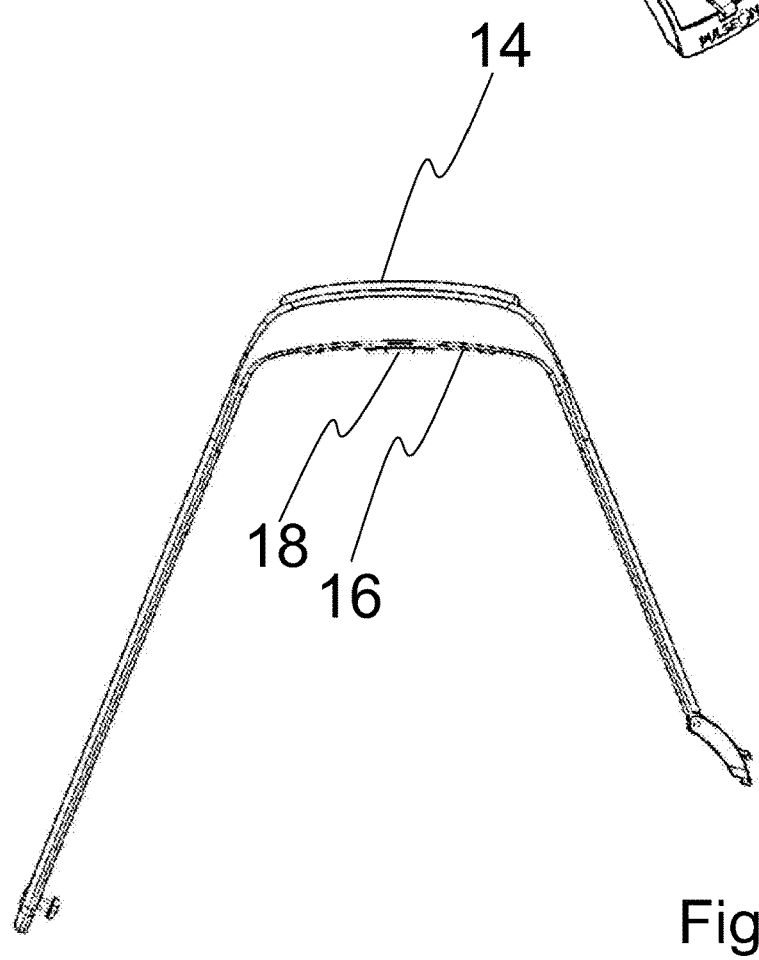
FIG. 8 shows a side view of an example of a biometric monitor attached to a silicone wrist strap

The pair of parts are located at two opposite perimeter side edges of the biometric monitor, and thereby defining a rotation axis (Ax1) extending in a first direction (Sx). The two opposite perimeter side edges refer to two opposite side edges of the flat or substantially flat monitor casing, arched or angular, usually on the sides of the casing being at the shortest distance apart from each other and/or on the side(s) having buttons or the like. This is schematically illustrated in FIGS. 1-6 and can also be seen in FIGS. 7-12 and 15-21 disclosing some exemplary embodiments. The rotation axis extends in a first direction which is a perpendicular direction to the direction of the strap. The rotation axis therefore allows planar movement or rotation of the biometric monitor in a plane perpendicular to the first direction. When the biometric monitor is attached to a wrist, the movement is mainly directed to the sensor area against the wrist. A second direction (Sy) perpendicular to the first direction (Sx) extends in the plane of the flat monitor casing. The strap is attached at the two sides of the casing along the second direction, as shown in FIG. 6.

The two opposite perimeter side edges discussed herein, which may be also called as the first perimeter side edge 40 and the second perimeter side edge 41, are marked in FIG. 6. Also two other opposite perimeter side edges, which are at different sides of the biometric monitor, which may be also called as the third perimeter side edge 42 and the fourth perimeter side edge 43, are marked in FIG. 6. In case of round or oval casing, the opposite perimeter side edges refer to opposite points of the perimeter.

The location of the rotation axis between the pair of parts is selected in such way that it extends above or across centre area or the sensor area in the bottom of the casing of the biometric monitor, i.e. the second side of the monitor. In one example, in the case of only one rotation axis, the rotation axis (Ax1) extends above or across centre point of the second side of the casing of the biometric monitor. This means that the perpendicular bisector (PB1) of the rotation axis (Ax1) between the pair of parts is at the biometric sensor area, i.e. inside the sensor area or the border defining the sensor area. This enables the sensor area to maintain contact with the user's wrist. The perpendicular bisector is a line segment perpendicular to a line between the pair of parts, or between the opposite perimeter side edges, and passing through the midpoint of said line. Such a midpoint is marked with an x in the FIG. 2 on the axis Ax1, and in FIG. 4 on the axes Ax1 and Ax2. The perpendicular bisector extends in a third direction (Sz) which is perpendicular to the first direction (Sx) and to the second direction (Sy), as shown in FIG. 5.

The term "centre area of the biometric monitor" refers to the area surrounding the centre of the flat side of the casing of the biometric monitor, i.e the centre of the first side or the second side of the biometric monitor. In case of the second side it may be called as the "centre area of the second surface". The centre refers to the centre point which is at the middle of two opposing perimeter sides of the monitor. When the sensor area is at the centre of the flat side of the casing of the biometric monitor, more particularly on the second side or surface, the "centre area" corresponds to the "sensor area". In such case the diameter of the centre area corresponds to the diameter of the sensor area. In one embodiment the diameter of the centre area is in the range of 5-20 mm, such as in the range of 8-15 mm, 10-15 mm, or 8-12 mm. In one example the centre area is circular.

FIGS. 1-4 illustrate schematic examples of the arrangements. In FIG. 1 a flat casing 12 contains a sensor area 18 on the second side 16 of the casing.

Figure 2:
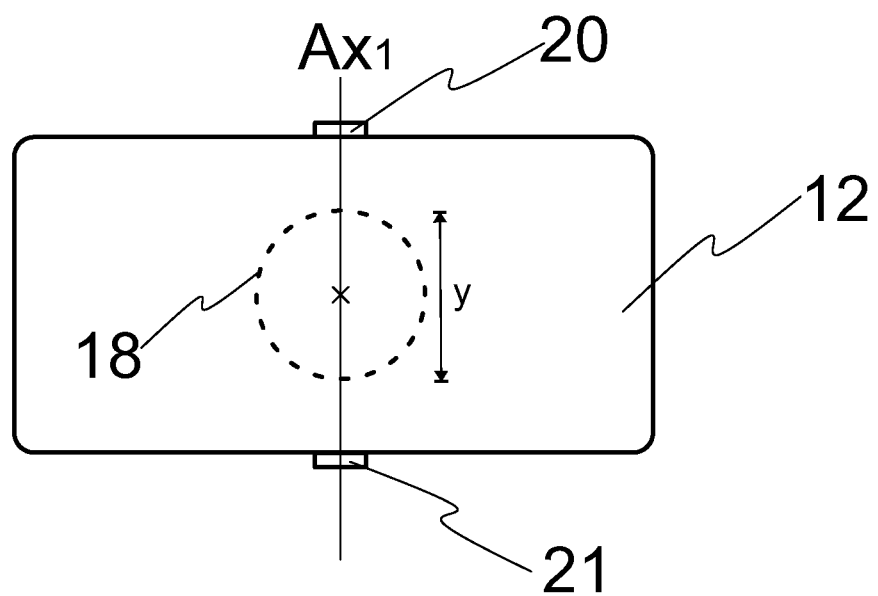
FIG. 2 shows a schematic view of a biometric monitor having one pair of parts seen from the sensor area side

In the illustrated example the sensor area 18 forms a protrusion or a bump, but the sensor area may be alternatively at the same level as the second surface 16, i.e. there is no protrusion. FIG. 2 shows two opposite perimeter side edges of the casing 12 having pair of parts 20, 21, one part on each perimeter side edge, which pair of parts define a rotation axis Ax1. The rotation axis Ax1 is located so that it overlaps or crosses the sensor area 18 on the second side or in practice extends above it in such way that the rotational movement along the rotation axis is directed to the sensor area. FIG. 1 shows that the perpendicular bisector PB1 of the rotation axis Ax1) between the pair of parts passes through the biometric sensor area 18. The diameter of the circular sensor area is marked as y.

In one embodiment the biometric monitor is attachable to the strap via two pair of parts 22, 23; 24, 25 enabling a rotational movement of the biometric monitor, the parts of each pair of parts being located at two opposite perimeter side edges of the biometric monitor, the two pair of parts thereby defining two parallel rotation axes Ax1, Ax2 extending in the first direction (Sx), wherein the perpendicular bisectors of the two parallel rotation axes (Ax1, Ax2) between the two pairs of parts are at the biometric sensor area.

One embodiment provides a biometric monitor comprising a casing having a first surface and a second surface opposite to the first surface, the second surface comprising a biometric sensor area, preferably located at the centre area of the second surface, and the monitor comprising two pairs of pivots being located at two opposite perimeter side edges of the biometric monitor, the biometric monitor being connected to a wrist strap, wherein the strap comprises a fork at the first end and a fork at the second end, each fork containing two protruding ends or parts having an aperture at each protruding end or part arranged to receive one pair of pivots of the biometric monitor, such that the biometric monitor is attached to the strap via the two pair of pivots defining two parallel rotation axes (Ax1, Ax2), enabling rotational movement of the biometric monitor, wherein the perpendicular bisectors of the two parallel rotation axes (Ax1, Ax2) between the two pairs of pivots pass through the biometric sensor area of the biometric monitor.

Figure 3:
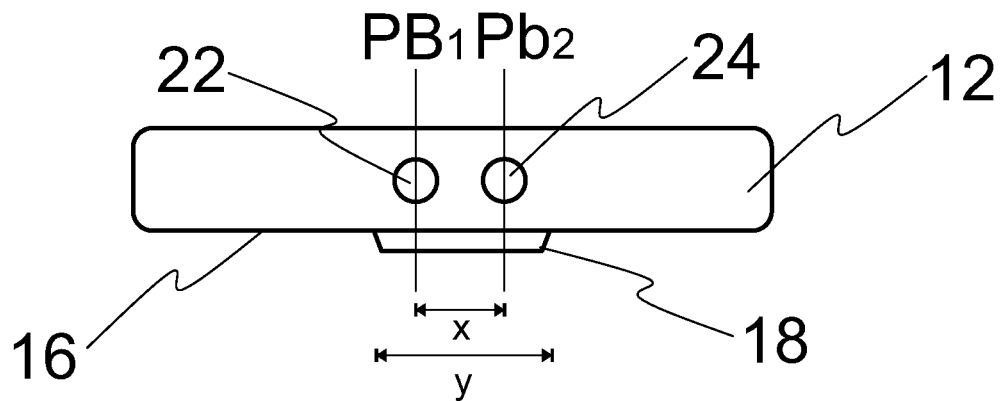
FIG. 3 shows a schematic side view of a biometric monitor with the directions Sy and Sz
Figure 4:
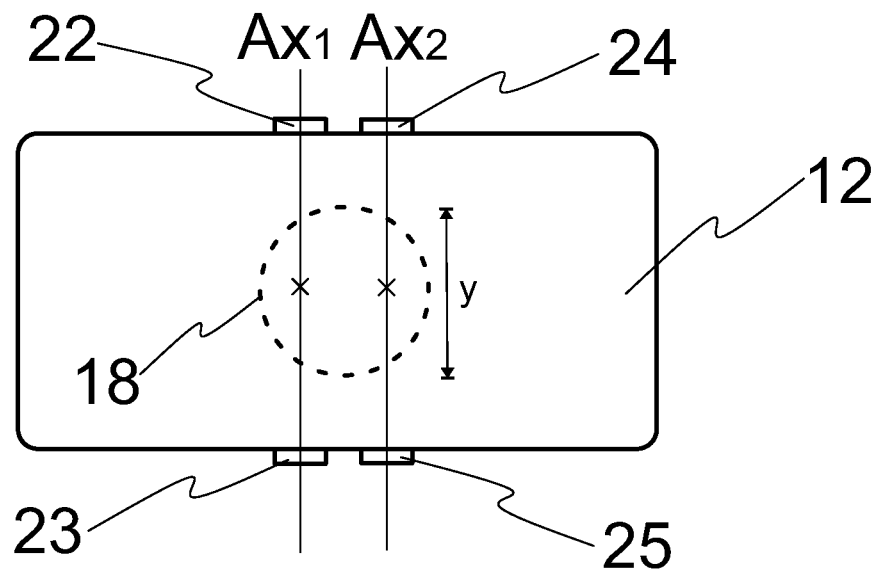
FIG. 4 shows a schematic side view of a biometric monitor with the directions Sx and Sy

FIG. 4 shows a schematic example of the two opposite perimeter side edges of the casing 12 having two pairs of parts 22, 24; 23, 25 which define two rotation axes Ax1, Ax2. The rotation axes Ax1, Ax2 are located so that they overlap or cross the sensor area 18 on the second side or in practice extend above it in such way that the rotational movement along the two rotation axes is directed to the sensor area (the points corresponding to the perpendicular bisectors are marked with crosses on the rotation axes Ax1, Ax2). FIG. 3 shows that the perpendicular bisectors PB1, PB2 of the rotation axes Ax1, Ax2 between the pair of parts pass through the biometric sensor area 18. The diameter of the circular sensor area is marked as y.

In such case the two parallel rotation axes are relatively close to each other in such way that they both extend above the sensor area on the second side of the casing. The distance x of the two parallel rotation axes Ax1, Ax2 is preferably equal to or less than the diameter y of the sensor area. The distance x of the two parallel rotation axes may be in the range of 5-20 mm, such as 5-15 mm, 5-10 mm, 10-15 mm, 8-15 mm, 5-12 mm or 8-12 mm, for example about 8 mm, about 9 mm, about 10 mm, about 11 mm or about 12 mm. In some examples, especially relating to embodiments having two-headed forked parts, the distance x of the two parallel rotation axes Ax1, Ax2 may be in the range of 10-20 mm, such as 14-18 mm or 15-16 mm, for example about 15 or 16 mm. In such case the diameter y of the sensor area may be for example 1-3 mm smaller than the distance x of the two parallel rotation axes Ax1, Ax2, such as diameter y being in the range of 12-14 mm.

Therefore the effective length of the biometric monitor attached to the strap is very short, and all the axes or the movements of the monitor are at the sensor area, which prevents the sensor area loosing contact with the skin of the user.

In one embodiment, as illustrated in the FIGS. 7-14, the receiving means comprises a frame 30 in an aperture 32 in the strap 10 connected to the strap via the pair of parts 20, 21. The aperture may be designed to fit to the biometric monitor, for example it may contain parts fitting to counterparts in the monitor casing, as can be seen in the FIGS. 11,13 and 14, which show only a strap arranged to receive the biometric monitor, but without the biometric monitor. In one embodiment, as also illustrated in the FIGS. 11, 13 and 14, the frame 30 comprises elastic material, such as elastomer, for example silicone, and it is designed in such way that a monitor casing may be pushed inside the frame by stretching the frame so that the casing will be securely fit into the frame when the elastic material is returned to the original shape. The frame may also be made of more rigid materials, which may however exhibit such an elastic function that the casing may be installed and secured. Such materials include plastics, composite materials and metals.

By definition, elasticity is the ability of a body to resist a distorting influence or deforming force and to return to its original size and shape when that influence or force is removed. Solid objects will deform when adequate forces are applied on them. If the material is elastic, the object will return to its initial shape and size when these forces are removed.

The frame 30 may be made of the same material as the strap, or it may be made of different material. In one embodiment the frame and/or the strap comprise or are made of elastic material, such as elastomeric material or elastomer. In one embodiment the elastic material is silicone. In one embodiment the elastic material is rubber. In one embodiment the elastic material is plastic. Also combinations of these or different materials may be used, and the strap may comprise both elastic and non-elastic materials. Different materials may be provided as layers, mixtures, or reinforcing portions, for example as laminates or composites. In one embodiment the frame and the strap comprise silicone, or are made of silicone. In addition to silicone they may also include reinforcing parts made of other materials, such as metal, plastics, composites and the like, such as nylon.

Examples of suitable silicones include silicone rubber. Uncured silicone rubber contains polymers of different chain lengths. It always comprises a principal silicon-oxygen chain (the siloxane backbone) and an organic moiety bound to the silicon. The properties of silicone rubber vary greatly depending on the organic groups and the chemical structure. The organic groups may be methyl, vinyl, phenyl or other groups. Examples of silicone polymers include MQ (polydimethylsiloxane PDMS), VMQ (polydimethylsiloxane in which a small number of methyl groups have been replaced by vinyl groups), PVMQ (VMQ in which a small number of methyl groups have been replaced by phenyl groups), and FVMQ (VMQ in which a small number of methyl groups have been replaced by trifluoropropyl substituents).

Uncured silicone rubber generally contains one or more crosslinkers, fillers and additives. A crosslinker, such as peroxide or platinum catalyst, is required to convert the raw silicone rubber into a mechanical stable cured product. Fillers are needed to reinforce the elastic silicone network. Examples of fillers include reinforcing fillers such as pyrogenic silica (generally with very high BET surface areas, such as more than 100 m$^2$/g), precipitated silica and carbon black; and non-reinforcing fillers such as quartz. Examples of additives include stabilizers, masticating aids and colorants.

One example of silicone is solid silicone rubber, which contains high molecular weight polymers having relatively long polymer chains. Another example of silicone is liquid silicone rubber, which contains polymers of lower molecular weight and shorter polymer chains.

The silicone parts may be manufactured by any suitable methods known in the art. In one example solid silicone rubber is molded by compression molding. Compression molding is a method of in which the molding material, generally preheated, is first placed in an open, heated mold cavity. The mold is closed with a top force or plug member, pressure is applied to force the material into contact with all mold areas, while heat and pressure are maintained until the molding material has cured. The process employs thermosetting resins in a partially cured stage, either in the form of granules, putty-like masses, or preforms. In another example liquid silicone is moulded by injection moulding. Injection moulding is method for producing parts by injecting material into a mould.

The elasticity or hardness of silicone may be measured with a durometer and expressed as Shore hardness, especially according to ASTM D2240 standard. The term durometer is often used to refer to the measurement as well as the instrument itself. There are several scales of durometer, used for materials with different properties. The two most common scales, using slightly different measurement systems, are the ASTM D2240 type A and type D scales. In one example the Shore A hardness of the silicone is in the range of 3-90.

The frame is connected to the at least one pair of parts. In one embodiment the frame is connected to one pair of parts. In one embodiment the pair of parts comprise elastic material, such as silicone. The pair of parts may be made of the same material as the frame and/or the strap, such as elastic material, for example elastomer. The elasticity of the elastic material of the pair of parts enables the rotational movement, i.e. no pivots or the like are required.

In one embodiment the strap contains one or more reinforcing parts embedded in the elastic material, such as metal or polymeric parts, for example thermoplastic polymer parts. The reinforcing parts may help maintaining the shape of the parts of the strap more rigid and to resist stretching or deformation, such as the frame, the pair of parts forming the hinges, and/or other parts. For example the frame may contain reinforced portions arranged to hold the biometric monitor module in a designed aperture even though the surrounding parts would be stretched, deformed or otherwise bent. Examples of reinforcing materials include thermoplastic polymers, such as Nylon, ABS and polycarbonate, or other thermoplastic polymers disclosed herein. Nylon is suitable to be used with silicones, because it tolerates high processing temperatures. The reinforcing materials may exhibit limited elasticity and bend in some degree, especially if present as thin enough structures. The reinforcing material should be selected to provide proper adhesion with the elastic material.

One specific embodiment, as illustrated in the examples of FIGS. 7-14, provides a wrist strap 10 for a biometric monitor, wherein the biometric monitor comprises a casing 12 having a first surface 14 and a second surface 16 opposite to the first surface, the second surface comprising a biometric sensor area 18 located at the centre area of the second surface, the centre area having a diameter in the range of 5-20 mm, said strap comprising a frame in an aperture in the strap, the frame and the strap comprising the same elastic material, the frame being arranged to receive the biometric monitor and being connected to the strap via a pair of elastic parts 20, 21 comprising the same elastic material as the frame and the strap and enabling rotational movement of the biometric monitor, the parts being located at two opposite perimeter side edges of the biometric monitor, and thereby defining one, more particularly only one, rotation axis Ax1, the rotation axis extending in a first direction which is a perpendicular direction to the direction of the strap, wherein the perpendicular bisector PB1 of the rotation axis Ax1 between the pair of parts is arranged to pass through the centre area of the second surface.

One embodiment provides a biometric monitor connected to a wrist strap, wherein the biometric monitor comprises a casing having a first surface and a second surface opposite to the first surface, the second surface comprising a biometric sensor area, said strap comprising a frame in an aperture in the strap containing the biometric monitor, the frame being connected to the strap via a pair of elastic parts enabling rotational movement of the biometric monitor, the parts being located at two opposite perimeter side edges of the biometric monitor, and thereby defining a rotation axis (Ax1), wherein the perpendicular bisector of the rotation axis (Ax1) between the pair of parts passes through the biometric sensor area of the biometric monitor. The sensor area may be located at the centre area of the second surface.

In one embodiment the receiving means comprise apertures arranged to receive the pair of parts in form of pivots. In such case the biometric monitor casing or module may contain the pivots, which are arranged to fit into a corresponding apertures in the strap.

Alternatively the biometric monitor casing or module contains the apertures and the strap contains the corresponding pivots. In one embodiment the receiving means comprise pivots arranged to be received by the pair of parts in form of apertures in the biometric monitor.

The strap may be a loop or it may be a strap having ends. The strap may have a lowest width in the range of 10-30 mm, for example 15-25 mm. Some portion(s) of the strap may be wider, such as a portion surrounding the biometric monitor, such as in the example of FIG. 10. In one embodiment the strap comprises a first end and a second end and contains two apertures at the first end and two apertures at the second end of the strap for receiving the pair of parts in form of pivots. In that case the first end and the second end refer to ends which are arranged to be connected to the biometric monitor. The strap may contain only one strap portion having the first end and the second end, as seen in FIGS. 7-11, wherein the ends are not connected to the biometric monitor. However the strap may contain more ends as well, for example if the strap is two-part strap containing a first strap portion and a second strap portion which may be fastened or connected by a buckle, clip, peg, or other fastening means. The FIGS. 15-20 show such two-part straps. The strap may contain at the first end and at the second end one or more connecting part(s) arranged to fit to the biometric monitor. The connecting part may be more rigid than the strap itself, and it may be made of different material(s). The connecting part may be a fork-like part or the like forked part, which contains two protruding parts, portions or ends arranged to be positioned at two opposite perimeter side edges of the biometric monitor, for example as shown in FIGS. 15-20. The forked part may contain a connecting end for connecting to a strap, which connecting end is at the opposite end of the forked part from the protruding ends. The connecting parts may be connected to the strap via a pivot, an axel, a pin or the like, preferably from a connecting end, to allow rotational movement, or they may be directly connected to the strap without any movable connecting part.

In one embodiment the strap contains a fork at the first end and a fork at the second end, each fork containing two protruding ends or parts having an aperture at each protruding end or part for receiving the pair of parts in form of pivots.

The protruding ends or parts refer to projections forming the fork and extending from the body 26, 27 of the fork. The fork has a first end containing the protruding parts or ends, and a second end wherefrom the fork is arranged to be connected to a strap, as is illustrated in FIGS. 15-21.

The connecting part may be designed so that it provides elasticity. This may be obtained by the choice of materials, and/or by the choice of the structure of the connecting part. For example plastic or composite materials may be relatively elastic as such, but also metal parts may be designed to provide elasticity. For example a fork having relatively narrow protruding portions made of metal may be expanded in such extent that the biometric monitor may be installed and/or removed from the connecting part by manually applying force.

In one embodiment the forks comprise a part providing elasticity allowing expanding of the fork to apply the pivots to the corresponding apertures, preferably the part comprising plastic, composite material, or metal. The fork may be formed of elastic material. Examples of plastic include thermoplastic polymers, such as acrylic (poly(methyl methacrylate), acrylonitrile butadiene styrene (ABS), Nylon, polylactic acid (PLA), polybenzimidazole, polycarbonalte (PC), polyether sulfone, polyetherether ketone, polyether imide, polyethylene (PE), polyphenyle oxide (PPO), polyphenylene sulphide (PPS), polypropylene (PP), polystyrene (PS), polyvinyl chloride (PVC) and polytetrafluoroethylene (PTFE). Examples of composite materials include plastic-fibre composite materials, such as composites of plastic and fibres selected from organic fibres, for example cellulose fibres, carbon fibres; or inorganic fibres, for example glass fibres, metal fibres, mineral fibres, and combinations thereof. Examples of metals include iron, steel, aluminium, titanium, silver, gold, and combinations or alloys thereof. A plastic or composite material may also contain reinforcing parts, such as metal parts or rigid parts made of different plastic or composite material.

In one embodiment the biometric sensor is an optical sensor. Other examples of biometric sensors include a temperature sensor, a potential sensor, a sound or an ultrasound sensor, an impedance sensor, a galvanic skin response sensor (GSR), an EKG sensor, an EMG sensor, and a wavelength sensor. The biometric monitor may contain one or more biometric sensor(s), for example two, three or four sensors. Also other sensors may be included, such as a GPS sensor, a magnetometer, or a motion detector, for example inertia, gyro or accelerometer. Usually the biometric sensor is located on the skin side or the user side of the monitor. In one example the portable biometric monitor contains an optical sensor and at least one sensor selected from a temperature sensor, a potential sensor, a sound or an ultrasound sensor, an impedance sensor, a galvanic skin response sensor (GSR), an EKG sensor, an EMG sensor, and a wavelength sensor. These sensors are directed towards the skin of the user, and they are arranged to detect one or more features from the user. Therefore such sensors are sensitive to the contact of the device with the user so the stability and other advantages provided by the strap attachment are especially advantageous for these sensor types. In one example the portable biometric monitor comprises an optical sensor and a galvanic skin response sensor. In one example the portable biometric monitor comprises an optical sensor and an impedance sensor.

Examples of possible physiological parameters to be monitored with the one or more biometric sensors in addition to heart rate include body temperature, blood pressure, blood flow, skin conductivity, tissue impedance, heart rate variability, motion, sleep, stress, fitness level, recovery level, effect of a workout routine on health, and caloric expenditure.

In one embodiment the portable biometric monitor is a heart rate monitor, or a pulse monitor. In one embodiment the portable biometric monitor is a heart rate monitor comprising an optical sensor, or an optical detector. The optical heart rate monitoring may be based on light scattering monitoring. In general an optical sensor includes one or more light or illumination sources for emitting light and one or more light or illumination detectors for detecting the light scattered or reflected from the user's body. Examples of the light sources include LED, laser and the like. Examples of the light detectors include photodiodes, phototransistors and the like. In one example the optical sensor comprises a light source and a light detector. In one example the optical sensor comprises two light sources and a light detector between the light sources, preferably all in a line. In one example the optical sensor comprises three light sources and two light detectors between the light sources, preferably all in a line. In one example the perpendicular bisector (PB1) of the rotation axis (Ax1) between the pair of parts passes through the light detector in the middle of the optical sensor array, or at least the perpendicular bisector of the rotation axis crosses the light detector in case it is not in the middle of the sensor area, to ensure that the optical sensor maintains contact with the skin. The light source(s) may emit light at one or more wavelength(s) or wavelength ranges. The light detector(s) may detect light at one or more wavelength(s) or wavelength ranges. Examples of such wavelength ranges include green spectrum, blue spectrum, red spectrum, and infrared spectrum. The light source(s) or the light detector(s) may further have a filter for filtering out undesired wavelengths. Examples of specific light sources having a specific wavelength range include green LED, blue LED, red LED, infra-red (IR) LED, near infra-red LED and combinations thereof. In general green light is suitable for the measurement of superficial blood flow in skin. Light with wavelengths between 500 and 600 nm (the green-yellow region of the visible spectrum) exhibits the largest modulation depth with pulsatile blood absorption. IR or near-IR wavelengths may be better for measurement of deep-tissue blood flow, such as blood flow in muscles. In one example the light source is an infra-red (IR) LED or a near infra-red LED.

In one example the light source is a green LED. A green LED has much greater absorptivity for both oxyhaemoglobin and deoxyhaemoglobin compared to for example infra-red light. Therefore, the change in reflected green light is greater than that in reflected infrared light when blood pulses through the skin, resulting in a better signal-to-noise ratio for the green light source. Infrared light may be used also to measure skin's moisture content on the absorption of infra-red light by the dermis, or for other purposes.

Figure 18:
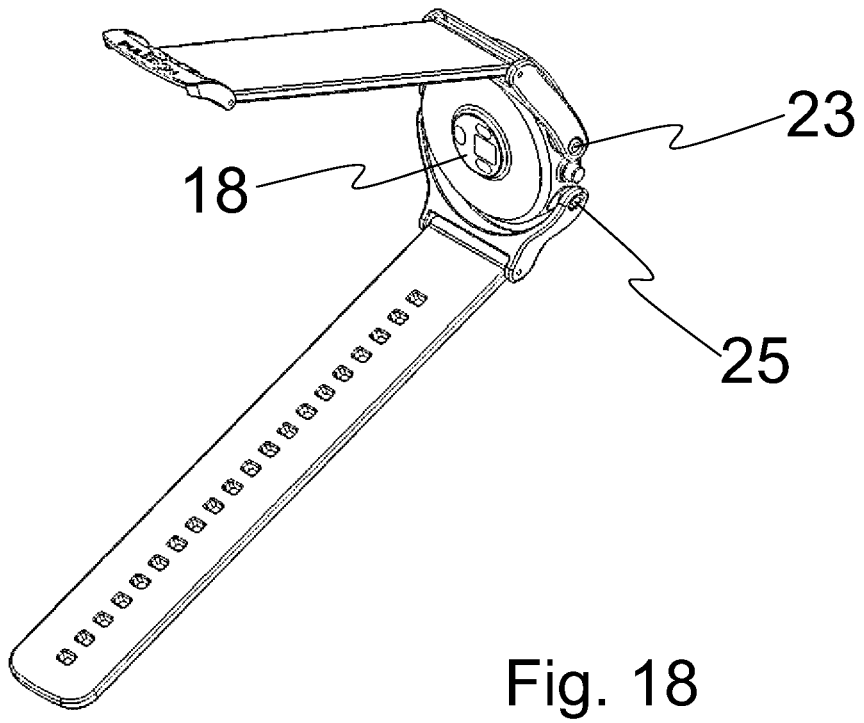
FIG. 18 shows an example of a biometric monitor attached to a wrist strap by two pair of parts seen from below

The biometric sensor, such as the optical sensor, is located at the second surface of the biometric monitor. More particularly the biometric sensor is mounted at the bottom of the monitor body, on the skin side of the user. The area at the second surface of the casing, housing or module of the biometric monitor, wherein the sensor elements are located, is called herein a sensor area. The sensor area may also correspond to the centre area of the biometric monitor. The sensor area usually overlaps the centre point of the second surface. The biometric sensor may form a protrusion of about 0.5-2 mm from the bottom of the monitor for anchoring the sensor to the skin, generally the protrusion having curved sides. The protrusion may form and/or define the sensor area, so that the diameter of the protrusion equals to the diameter of the sensor area. Usually this is on the opposite side of the monitor body in relation to the display, if present. In one example the sensor does not form a protrusion, i.e. the bottom of the monitor is flat or substantially flat. In any case the biometric sensor area may be determined as an area containing one or more elements of the sensor, such as one or more light source(s) and one or more light detector(s) in the case of an optical sensor. The biometric sensor area may be also called as biometric sensor. The sensor area may be circular, as shown in FIGS. 2, 4, and 18, or it may have another shape, for example it may be rectangular. The diameter y of the sensor area may be in the range of 5-20 mm, more particularly in the range of 8-15 mm, 10-15 mm, or 8-12 mm. In a case of a non-circular sensor area the diameter refers to the shortest diameter, such as the distance of two opposite straight edges. The diameter y of the sensor area, especially in the case of no protrusion, may also refer to a longest distance between the peripheral edges or perimeters of the sensor elements, for example the peripheral edges or perimeters of two light sources having a light detector in-between, as shown in FIG. 18. The diameter y is therefore intended to cover the elements of the biometric sensor. Preferably the distance y of the sensor area is determined in the second direction (Sy).

The bottom of the casing may contain one hole or aperture for the optical sensor as a whole, or separate holes or apertures for the light source(s) and for the light detector(s), or for other types of sensors, emitters and/or detectors. The apertures may contain lenses or other transparent material, or the optical sensor(s) and the light source(s) may be installed into the apertures.

More precisely the optical heart rate monitoring is implemented by irradiating the skin of the user with visible or infrared light generated by said light source. The light source is generally arranged in close contact with the skin of the user. A light detector is arranged also in close contact with the skin in a nearby location and it is arranged to detect and measure the light resulting from reflection, absorption and/or scattering by the skin. The variations in said detected and measured values allow the measurement of the flow of oxy- and deoxyhemoglobin and the expansion of blood vessels. A photoplethysmogram (PPG) may be obtained. This enables for example oxymetric and pulsometric measurements, which may be further used to define the heart rate of the user.

In addition to heart rate, an optical sensor may be configured to monitor the user's respiration, heart rate variability, oxygen saturation ($SpO_2$), blood volume, blood glucose, skin moisture and/or skin pigmentation level.

The biometric monitor generally includes one or more processors, memory, one or more biometric sensors, an interface, and optionally a display arranged to present information, operatively connected together. The biometric monitor naturally contains a power source, for example a battery and/or a solar cell. The one or more processor(s) is/are configured to process the biometric information which is measured by the one or more sensors, to determine an output from the measurement. The one or more processor(s) is/are usually a comprised in a control unit or in means for controlling the biometric monitor. The determined information may be outputted to a display, or the information may be sent to an external device wirelessly connected to the biometric monitor, for example by using Bluetooth, WiFi, cellular or any other suitable wireless technology. In such case the biometric monitor contains means for wireless communication, such as a transmitter and a receiver configured to communicate with the external device. One or more of the one or more processors, the memory, one or more biometric sensors, the interface, the transmitter/receiver and the display arranged to present information are usually implemented as one or more electronic circuit boards and/or modules. The device may also contain audio means for outputting and/or inputting sound, for example as a part of the user interface. All the parts discussed herein are included in the same casing.

The display may use one or more of any of the suitable display technologies including LED, LCD, OLED, AMO-LED, E-Ink, Sharp display technology, graphical display, and other suitable display technologies. This display may be used to present data acquired or stored locally on the device or data acquired remotely from other devices or Internet services.

The external device may be a mobile terminal, for example a handheld device such as a mobile phone, a phablet or a tablet, or a computer, for example as a portable computer or any other computer, or any other suitable external device. The information may be processed and/or displayed in the external device, for example the information may be collected, saved, processed and analyzed. Other types of information may also be combined with the measured biometric information, such as geographic information for example obtained from a GPS system in the device itself or in the external device, time information, temperature information, and the like. The other information may be measured using the same device or the other information may be obtained from another source or device, such as the external device. The combined information may be processed to a presentable form, for example to present statistical information as graphs or tables.

The interface may comprise a user interface for indicating the state of one or more data types measured and/or analyzed. The user interface may include one or more physical buttons and/or a touch sensitive screen as means for controlling the device and/or interacting with it, or a combination thereof. The interface may also comprise means for communicating with an external device by using wireless technology. The interface may also comprise means for presenting information on a display.

Next the embodiments will be described with a reference to exemplary implementations of biometric monitors and wrist straps.

EXAMPLES

Example 1

Figure 11:
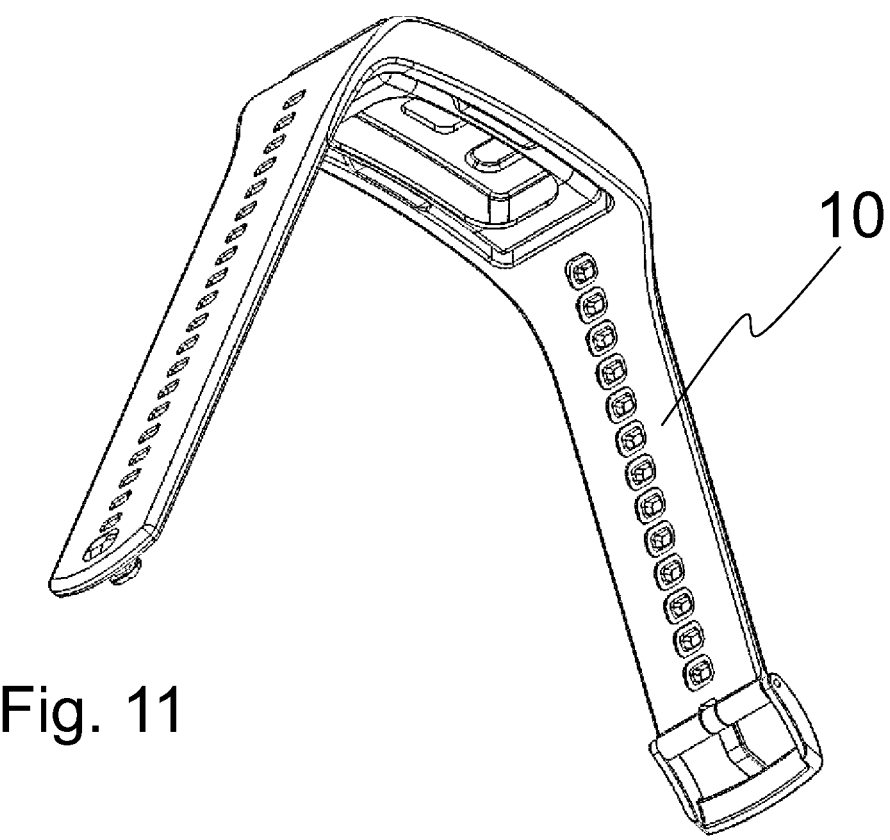
FIG. 11 shows an example of a silicone wrist strap without the biometric monitor module
Figure 13:
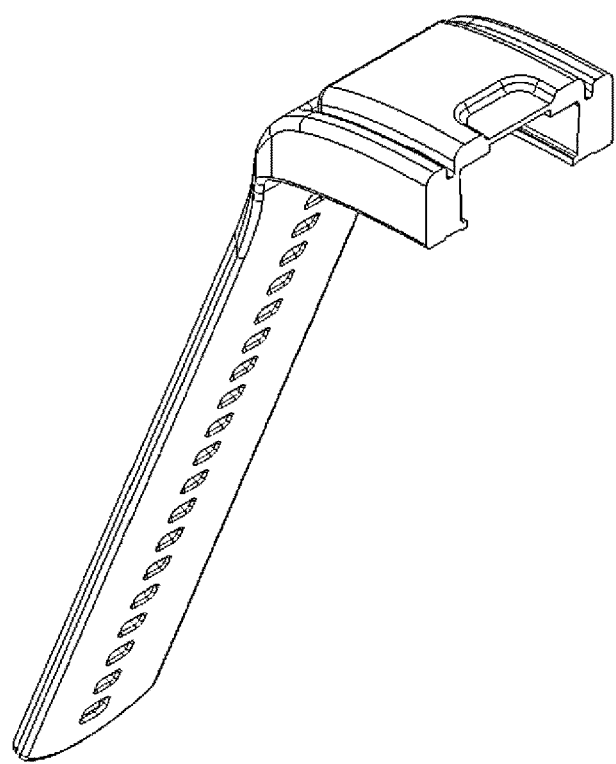
FIG. 13 shows an example of a cross section of a silicone wrist strap without the biometric monitor module
Figure 14:
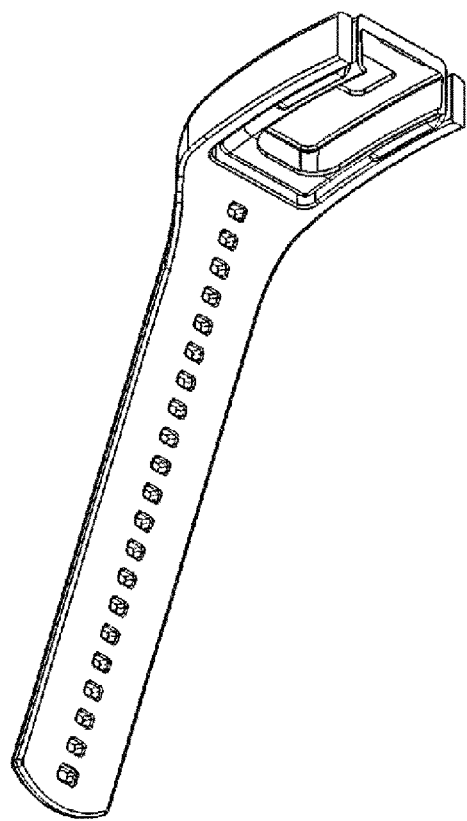
FIG. 14 shows an example of a cross section of a silicone wrist strap without the biometric monitor module seen from below
Figure 15:
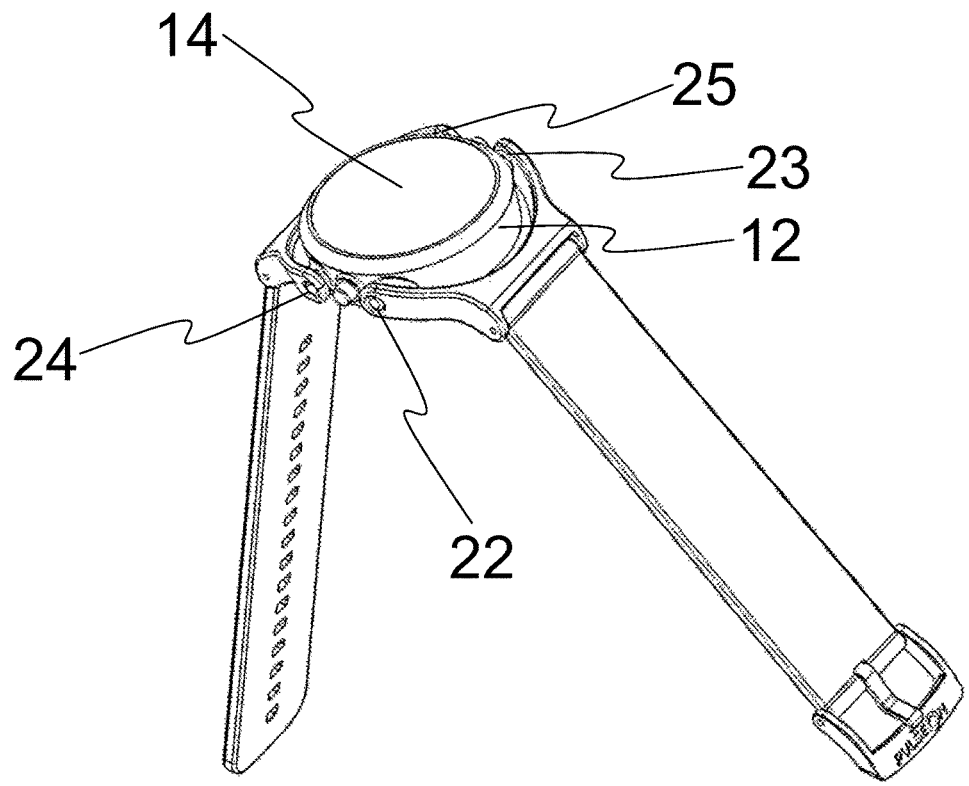
FIG. 15 shows an example of a biometric monitor attached to a wrist strap by two pair of parts
Figure 16:
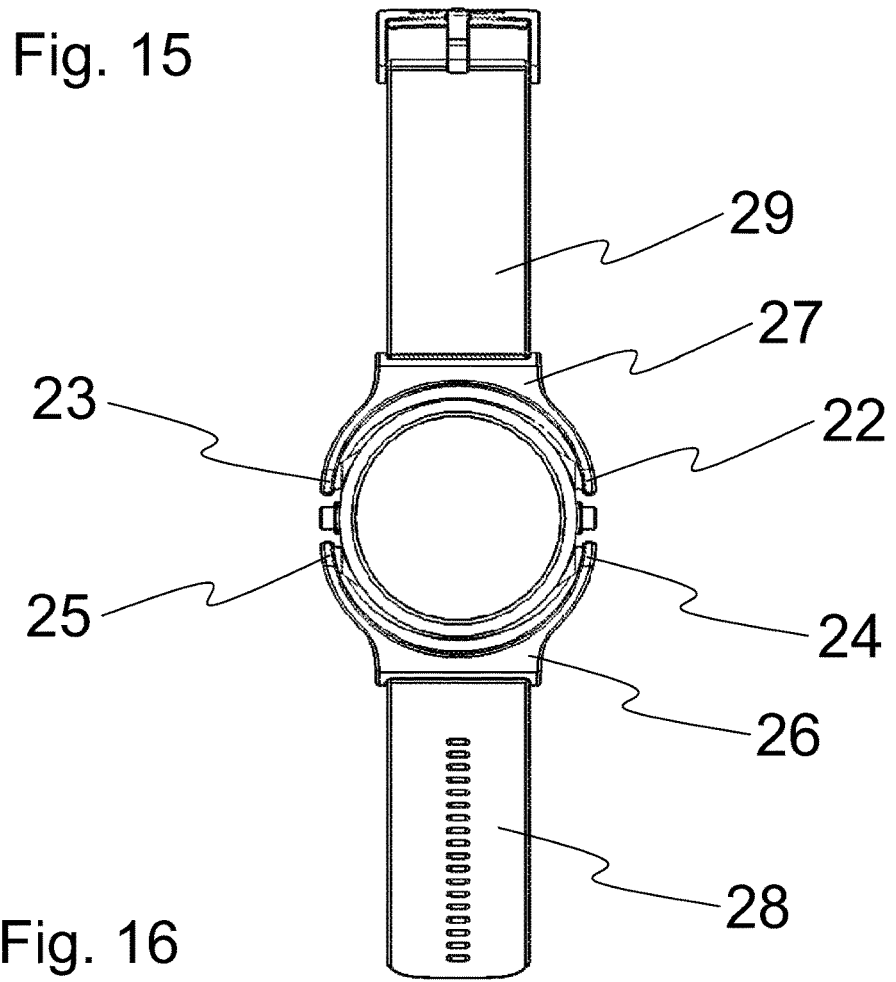
FIG. 16 shows an example of a biometric monitor attached to a wrist strap by two pair of parts seen from above

A silicone wrist strap 10 is provided as shown in FIG. 11. The strap comprises a buckle at the one end and corresponding plurality of apertures arranged to receive the tongue of the buckle at the other end so that the strap may be attached to a wrist of a user and fastened to obtain a desired diameter. As can be seen from FIG. 11 the strap comprises a frame with an aperture which is open at the skin side of the strap so that a biometric monitor module may be installed into the aperture. The aperture has flexible parts which may be stretched so that the module may be threaded into the aperture. The FIGS. 13 and 14 show the structure of the frame and the aperture therein, which forms a compartment adapted to receive the module.

Figure 9:
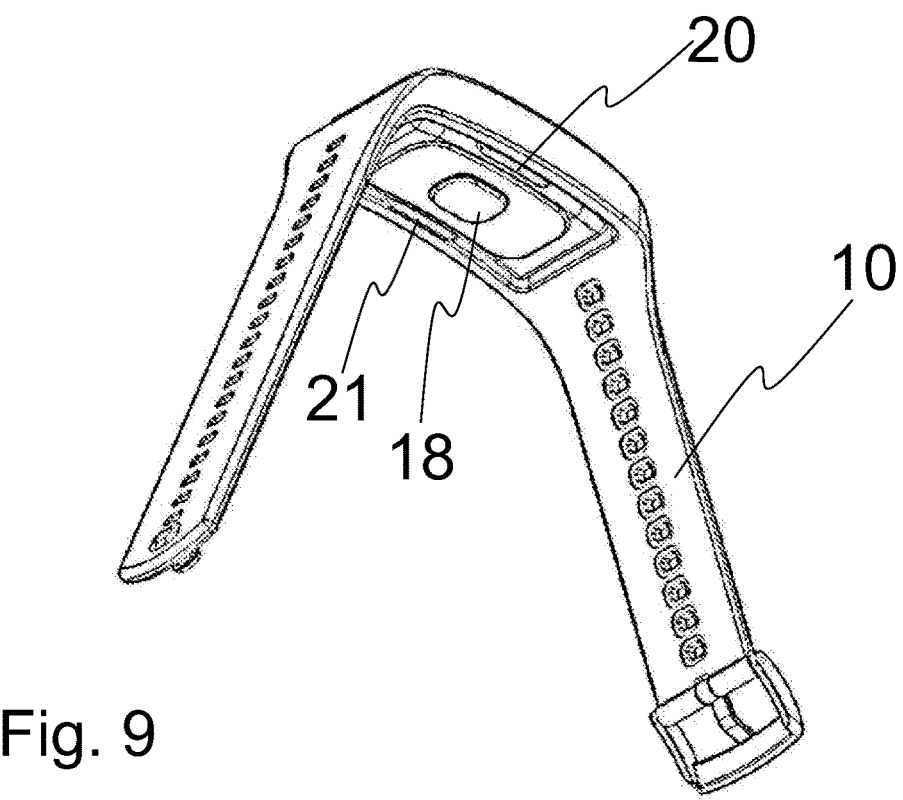
FIG. 9 shows an example of a biometric monitor attached to a silicone wrist strap seen from below
Figure 10:
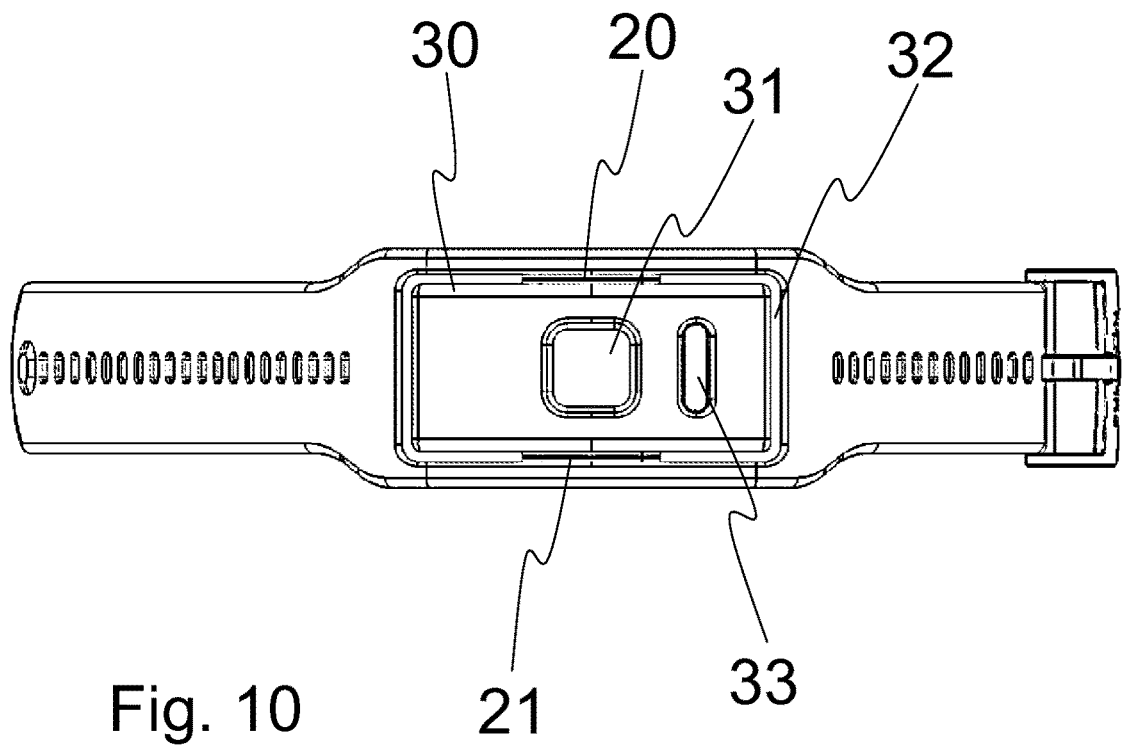
FIG. 10 shows an example of a biometric monitor attached to a silicone wrist strap seen from above
Figure 12:
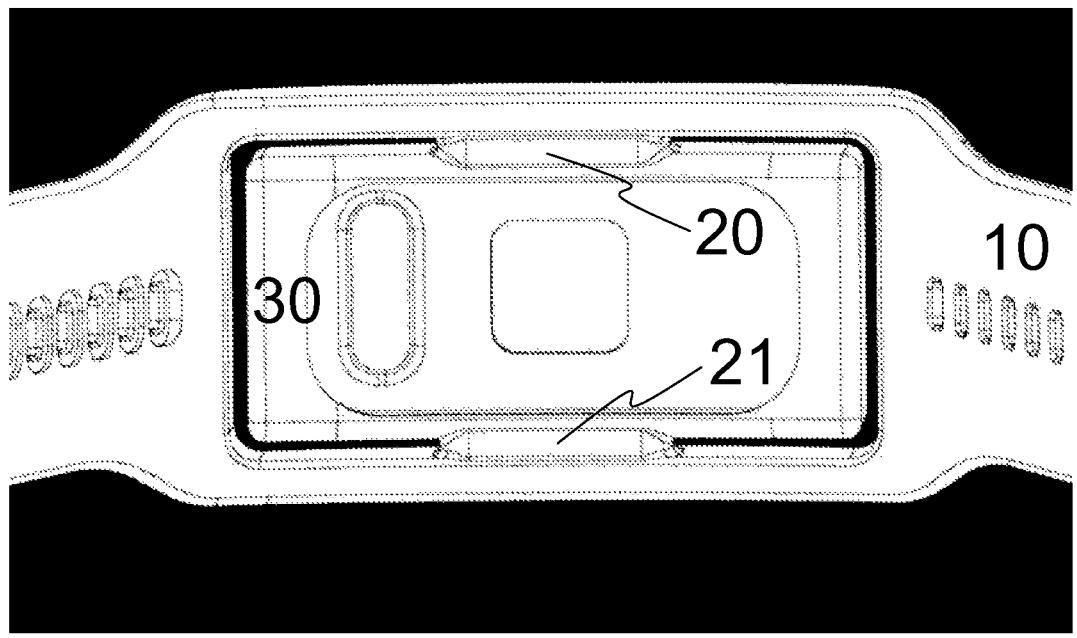
FIG. 12 shows a close view of an example of the hinged frame part of the biometric monitor attached to a silicone wrist strap

FIG. 9 shows the same wrist strap with the module installed into the aperture wherein the module is securely fitted. The frame 30 which contains the aperture for the module is connected to the silicone strap with a pair of parts 20, 21, as can be seen in FIG. 12. These parts are formed of the same elastic material as the frame and the strap, the silicone, and therefore the pair of parts enable rotational movement of the module installed into the frame. The frame 30 is connected to the strap only by the pair of parts 20, 21 and is otherwise freely movable as there is a narrow opening 32 between the frame 30 and the strap 10.

On the top of the strap, which is the opposite side that what is against the skin during the use, there are two apertures or recesses 31, 32 which enable pushing a button or other touchable area in the module through the aperture or the recess having a thin layer of silicone in the bottom. The apertures or recesses may also enable seeing a display or a light source in the module.

The pair or parts 20, 21 are at the both sides of the sensor area 18 as can be seen in FIG. 9. The rotation axis Ax1 between the parts 20, 21 crosses the sensor area, so the module can only move in such way that any rotational movement of the module is on the sensor area. As the strap is tightened against the skin of the user, the sensor area practically swings on the sensor area keeping it continuously against the skin, and only the far edges of the module may lose contact with skin.

Example 2

A biometric monitor having a round casing 12 is provided as shown in the FIGS. 15-18. The casing is attached to a two-part strap 28, 29 having a width of 20 mm and thickness of 2.3 mm, the strap being connected via forks 26, 27 to two pairs of parts 22, 23; 24, 25, which contain pivots in the casing, which are connected to apertures in the two-headed forked parts 26, 27 attached to the strap parts 28, 29. The forks have two protruding parts in an arched shape, which surround the circular casing of the biometric monitor. The forks may be bent by hands to that the pivots on the casing may be removed from the apertures in the ends of the forks, so that the casing may be removed from the strap. Similarly the forks may be attached to the pivots manually to attach the casing to the strap. Between the parts 23, 25; 22, 24 at each perimeter side edges of the casing there are buttons for operating the biometric monitor. The pivots secure the buttons so that the risk of pushing the buttons accidentally is decreased.

Figure 17:
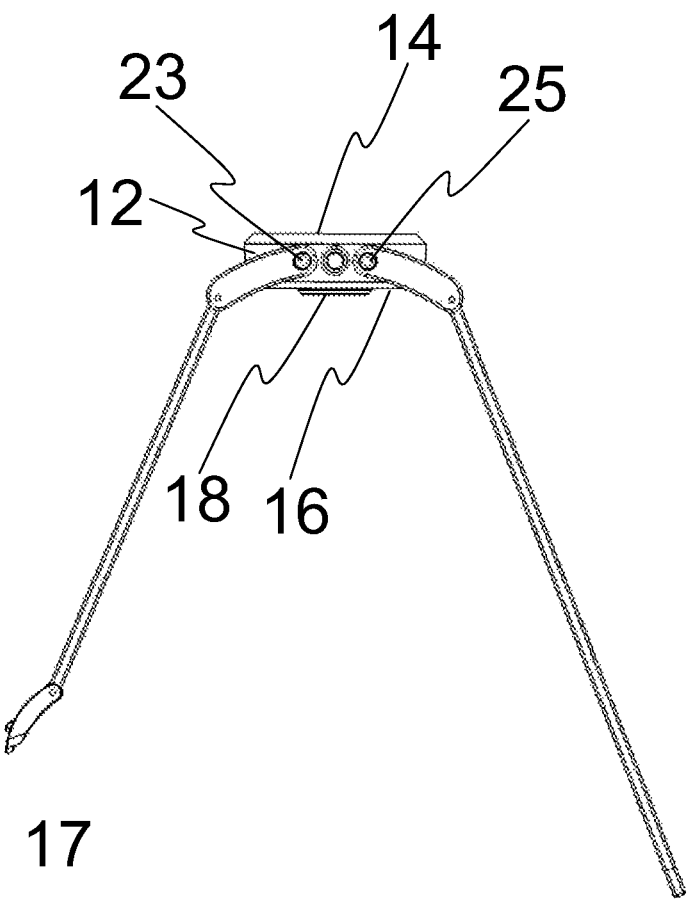
FIG. 17 shows a side view of an example of a biometric monitor attached to a wrist strap by two pair of parts

The two pairs of parts form two parallel rotation axes (Ax1, Ax2) between the two pairs of parts 22, 23; 24, 25, wherein the rotation axes cross the biometric sensor area 18 above it, especially as seen in FIG. 17. This allows rotational movement of the casing 12 along the two rotation axes in such way that the movement is on the sensor area. As the strap is tightened against the skin of the user, the sensor area practically swings on the sensor area keeping it continuously against the skin, and only the far edges of the casing may lose contact with skin.

Example 3

Figure 19:
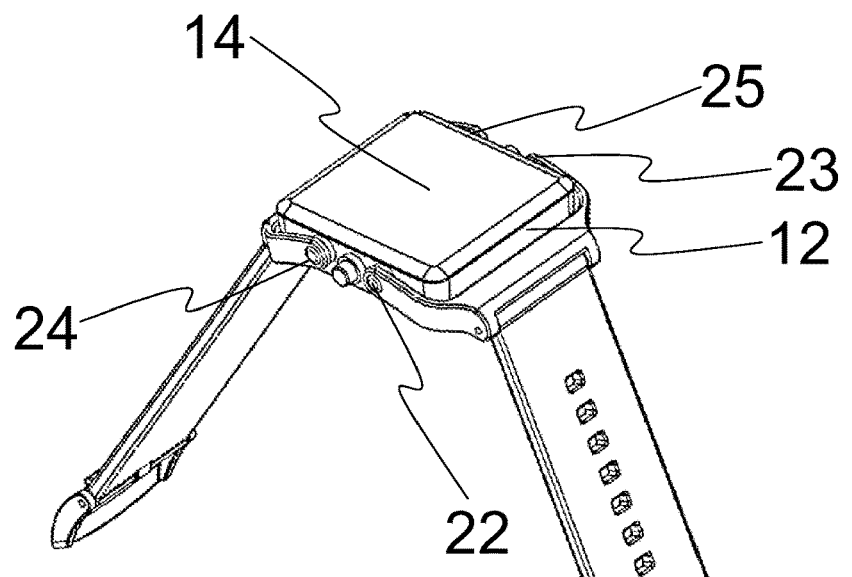
FIG. 19 shows an example of a biometric monitor attached to a wrist strap by two pair of parts
Figure 20:
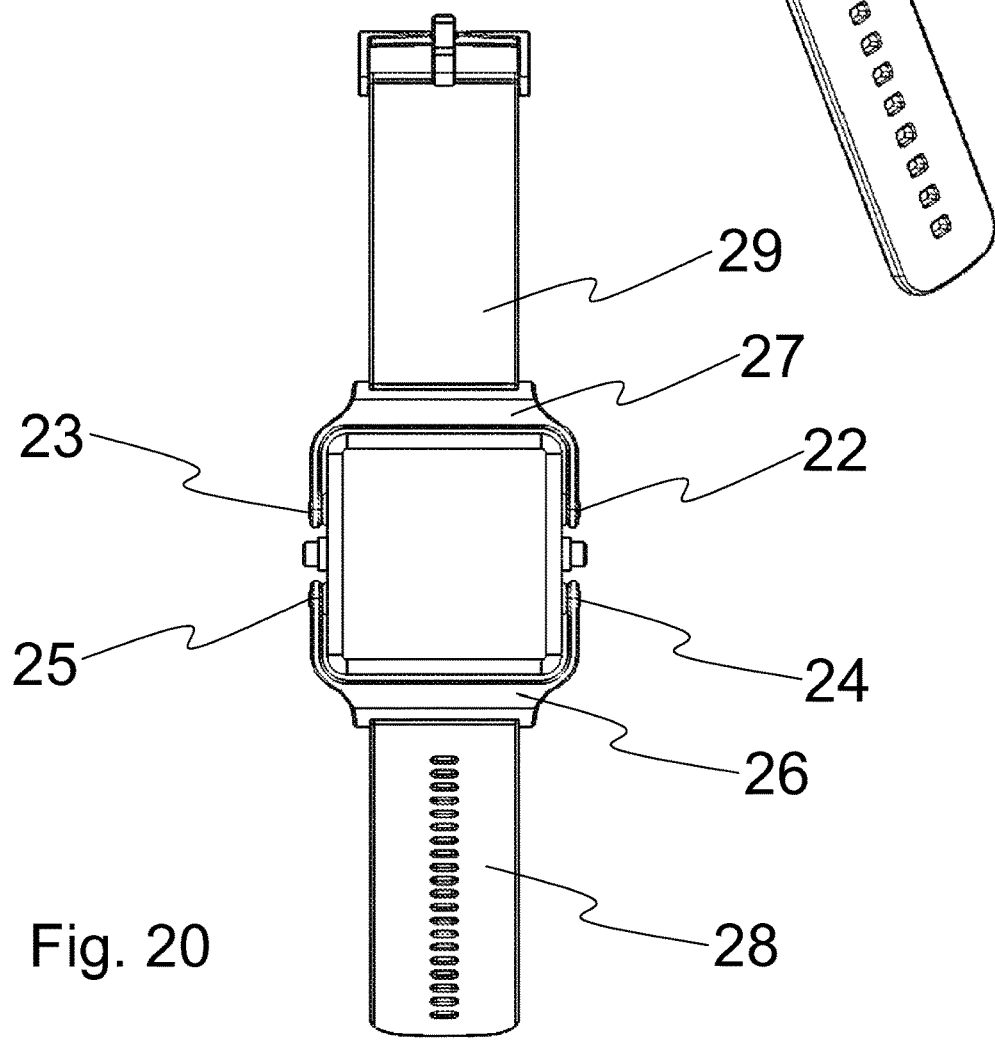
FIG. 20 shows an example of a biometric monitor attached to a wrist strap by two pair of parts seen from above

A biometric monitor having a square-shaped casing having dimensions of 32.0 mm×31.5 mm×10.9 mm is provided as shown in FIGS. 19 and 20. The structure is otherwise similar to the structure of Example 2, but the forked parts 26, 27 have a different shape.

Example 4

Figure 21:
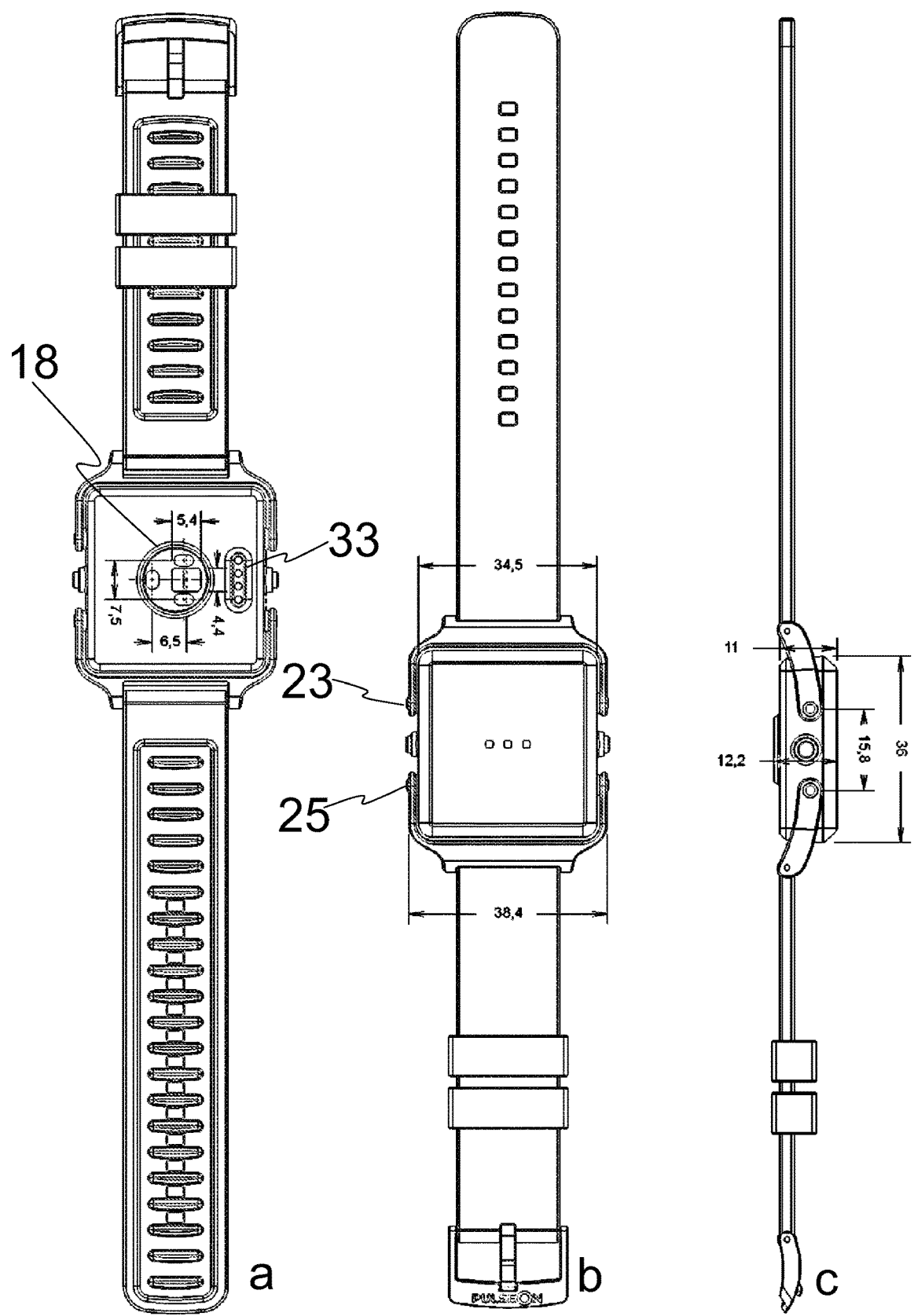
FIG. 21 shows an example of a biometric monitor attached to a wrist strap by two pair of parts seen from a) below, b) above and c) side.

A biometric monitor similar to the ones described in Examples 2 and 3 having a square-shaped casing but having dimensions of 36.0 mm×34.5 mm×12.2 mm is provided as shown in FIGS. 21 *a-c*. The forks have two protruding parts in an angular shape, which surround the four-cornered casing of the biometric monitor. The two protruding parts or ends are at the one end of the fork, the other end of the fork being connected to the strap.

The distance x of the two parallel rotation axes is 15.8 mm. The diameter y of the sensor area at the bottom of the device is 13 mm at the top of the sensor area. The sensor area comprises three light sources, wherein two light sources are at 7.5 mm distance from each other with a light detector of 5.4×4.4 mm between them. These two light sources and the light detector are in a line, and a third light source is located at a distance of 6.5 mm from the line to a perpendicular direction to the line from the middle of the light detector. This construction and dimensions were found to be optimal for this type of device.

At the bottom of the device there is also an electrical connector 33 comprising four pins, two for power and two for data transfer. Both the sensor area and the connector are between the two rotation axes (Ax1, Ax2).

The invention claimed is:

1. A wrist strap for a biometric monitor, comprising:
 a strap formed in one-piece and having two ends, the strap comprising an aperture between the two ends and wherein the strap comprises a first elastomeric material; and
 a frame enclosed in the aperture in the strap, wherein the frame is a polygonal shape having a top side and an opposing bottom side, a first side and an opposing second side, and a third side and an opposing fourth side, and wherein the frame comprises a second elastomeric material; the frame being arranged to receive and removably attach the biometric monitor to the strap, wherein the frame is arranged to receive the biometric monitor inside the frame by stretching the frame so that the biometric monitor securely fits into the frame when the elastic second elastomeric material is returned to the original shape; and the frame being connected to the strap via a single pair of parts comprised in the aperture in the strap enabling rotational movement of the biometric monitor, wherein one of the parts being located on the third side and the other one of the parts being located on the opposing fourth side of the frame, and thereby defining a rotation axis between the single pair of parts, wherein the parts do not extend into and through the frame or strap, the rotation axis extending in a first direction which is a perpendicular direction to the direction of the strap, wherein a perpendicular bisector of the rotation axis between the single pair of parts is arranged to pass through a centre area of the frame, wherein the frame in the aperture is connected to the strap only by the single pair of parts and the frame is otherwise freely rotatable around the rotation axis, wherein the strap does not rotate about the rotation axis;
 wherein the single pair of parts comprises a third elastomeric material.

2. The wrist strap of claim 1, wherein the first elastomeric material and the second elastomeric material are the same, wherein the frame and the strap contain reinforced parts embedded in the second elastomeric material and the first elastomeric material, respectively.

3. The wrist strap of claim 2, wherein the first elastomeric material and the second elastomeric material are is a silicone, and the strap contains one or more reinforcing parts embedded in the silicone.

4. The wrist strap of claim 1, wherein the diameter of the centre area is in the range of 8-15 mm.

5. The wrist strap of claim 1, wherein the diameter y of the sensor area is 1-3 mm smaller than the distance x of the rotation axes.

6. The wrist strap of claim 1, wherein the first elastomeric material, the second elastomeric material, and the third elastomeric material are the same.

7. A wearable device, comprising:
 a biometric monitor comprising a casing having a first surface and a second surface opposite to the first surface, the second surface comprising a biometric sensor area located at the centre area of the second surface, the centre area having a diameter in the range of 5-20 mm, and a wrist strap comprising:

a strap formed in one-piece and having two ends, the strap comprising an aperture between the two ends and wherein the strap comprises a first elastomeric material; and a frame enclosed in the aperture in the strap, wherein the frame is a polygonal shape having a top side and an opposing bottom side, a first side and an opposing second side, and a third side and an opposing fourth side, and wherein the frame comprises a second elastomeric material; the frame being arranged to receive and removably attach the biometric monitor to the strap, wherein the frame is arranged to receive the biometric monitor inside the frame by stretching the frame so that the biometric monitor securely fits into the frame when the elastic second elastomeric material is returned to the original shape; and the frame being connected to the strap via a single pair of opposing parts comprised in the aperture in the strap enabling rotational movement of the biometric monitor, wherein one of the parts being located on the third side and the other one of the parts being located on the opposing fourth side of the frame, and thereby defining a rotation axis between the single pair of parts, wherein the parts do not extend into and through the frame or strap, the rotation axis extending in a first direction which is a perpendicular direction to the direction of the strap, wherein a perpendicular bisector of the rotation axis between the single pair of parts is arranged to pass through a centre area of the frame, wherein the frame in the aperture is connected to the strap only by the single pair of parts and the frame is otherwise freely rotatable around the rotation axis, wherein the strap does not rotate about the rotation axis, and wherein the biometric monitor is connected to the wrist strap; and wherein the single pair of parts comprises a third elastomeric material.

8. The biometric monitor of claim 7, wherein the single pair of parts comprise a single pair of elastic parts.

9. The biometric monitor of claim 7, wherein the biometric sensor area comprises an optical sensor.

10. The biometric monitor of claim 9, wherein the biometric monitor is arranged to obtain a photoplethysmogram (PPG).

* * * * *